United States Patent [19]

Bridges et al.

[11] Patent Number: 5,393,360
[45] Date of Patent: Feb. 28, 1995

[54] METHOD AND APPARATUS FOR COMBINING A TENSIONED ELASTIC GARTER WITH A SUBSTRATE

[75] Inventors: Russell P. Bridges; James R. Golan; Ronald H. Helton; Stephen J. Lange, all of Cincinnati; Michael J. Madil, Wyoming; Michael G. Nease, Fairfield, all of Ohio

[73] Assignee: The Procter & Gamble Company, Cincinnati, Ohio

[21] Appl. No.: 132,730

[22] Filed: Oct. 6, 1993

[51] Int. Cl.⁶ .............................................. A61F 13/15
[52] U.S. Cl. ................... 156/73.3; 156/73.1; 156/160; 156/229; 156/251; 156/267; 156/494; 156/495; 156/515; 156/522; 156/552; 156/567; 156/580.1
[58] Field of Search ............... 156/160, 161, 251, 267, 156/73.1, 73.3, 580.1, 580.2, 494, 495, 513, 514, 515, 518, 522, 530, 552, 567, 556, 308.4, 229

[56] References Cited

U.S. PATENT DOCUMENTS

| | | | |
|---|---|---|---|
| 2,490,451 | 12/1949 | Magid | 156/161 |
| 2,768,107 | 10/1956 | Magid | 156/160 |
| 2,957,792 | 10/1960 | Magid | 156/251 |
| 3,225,764 | 12/1965 | Magid | 156/251 |
| 3,505,149 | 4/1970 | Sanchez | 156/160 |
| 3,562,041 | 2/1971 | Robertson . | |
| 3,657,033 | 4/1972 | Sager | 156/73.3 |
| 3,679,526 | 7/1972 | Horton . | |
| 3,681,176 | 8/1972 | Reifenhauser et al. . | |
| 3,733,238 | 5/1973 | Long et al. . | |
| 3,737,361 | 6/1973 | Obeda . | |
| 3,764,442 | 10/1973 | Parry . | |
| 3,852,144 | 12/1974 | Parry . | |
| 3,973,066 | 8/1976 | Smith, II et al. . | |
| 4,157,719 | 6/1979 | DeWoskin | 156/73.3 X |
| 4,227,959 | 10/1980 | Brown . | |
| 4,496,407 | 1/1985 | Lowery, Sr. et al. | 156/88 X |
| 4,610,750 | 9/1986 | Mango | 156/73.3 X |
| 4,630,429 | 12/1986 | Christine . | |
| 4,743,241 | 5/1988 | Igaue et al. . | |
| 4,767,482 | 8/1988 | Diez et al. . | |
| 4,786,346 | 11/1988 | Ales et al. | 156/160 |
| 5,059,277 | 10/1991 | Willhite, Jr. et al. . | |
| 5,080,741 | 1/1992 | Nomura et al. . | |
| 5,110,399 | 5/1992 | Yoshida et al. . | |
| 5,147,487 | 9/1992 | Nomura et al. . | |
| 5,213,645 | 5/1993 | Nomura et al. . | |
| 5,236,430 | 8/1993 | Bridges . | |
| 5,275,676 | 1/1994 | Rooyakkers et al. . | |

FOREIGN PATENT DOCUMENTS

464865   8/1992  European Pat. Off. .
WO 94/06384  3/1994  WIPO .

Primary Examiner—Jeff H. Aftergut
Attorney, Agent, or Firm—Ronald W. Kock; John M. Howell; Kevin C. Johnson

[57] ABSTRACT

A method and apparatus for forming a tensioned garter and bonding it to a substrate while holding the garter in a predetermined shape. A garter is any continuous loop of elastic material or a laminate of elastic bands and one or more flexible backing sheets. In one embodiment mandrels having a perimeter of the desired garter shape are mounted to a rotating drum. Tensioned elastic ribbons are progressively wrapped, sealed, and cut around the mandrels to form individual tensioned garters which cling to the side walls of the mandrels. In another embodiment each mandrel has a top surface. The upper portion of a garter has sufficient elastic tension to cause it to fold over the mandrel top surface to form a garter flange thereon. A substrate is then engaged with the garter flange and an external sealing means seals the flange to the substrate, using the mandrel top surface as an anvil. In still another embodiment the mandrel top surface has a raised outer rim. An ultrasonic horn seals a garter flange to a substrate where they are supported by the mandrel rim. The mandrel rim is shaped to provide a continuous seal which is weakened at its inner edge. When the weakened edge is broken, substrate and garter materials inside the seal edge are removed, thereby forming a hole around which the remaining portion of the garter may contract. Vacuum is applied from the mandrel top surface to the substrate inside the garter in this embodiment in order to break the seal edge and remove this material as the substrate and garter are stripped off the mandrel.

5 Claims, 7 Drawing Sheets

METHOD AND APPARATUS FOR COMBINING A TENSIONED ELASTIC GARTER WITH A SUBSTRATE

FIELD OF THE INVENTION

The present invention relates to a process for elasticizing an article by bonding a tensioned elastic member to it, and more particularly to a process wherein the elastic member is a garter stretched in more than one direction and the article is a substrate. Even more particularly, the present invention relates to a process wherein a tensioned elastic garter is held in a predetermined shape by a mandrel as it is bonded to a substrate.

BACKGROUND OF THE INVENTION

Elasticizing a flexible substrate, such as a sheet of cloth or plastic film, may be accomplished by attaching a tensioned elastic member to it. When the elastic member is allowed to contract, the flexible article wrinkles or shirrs to contract in dimension along with the elastic member. The article can subsequently be stretched as though it were itself elastic. This concept is used, for example, in the manufacture of disposable diapers to provide elastic leg cuffs for snug, leak-resistant, body fit. There are many commercial processes for combining elastic members with substrate materials. However, reliably combining tensioned elastics with a continuously moving substrate web, as is required in high speed diaper-making systems, has required relatively complex methods and apparatii. If, for example, elasticity is needed only in machine direction (the direction of travel of a continuously moving web), a continuous elastic ribbon may be fed parallel to the direction of substrate web travel from a source metering the elastic ribbon at a lower rate of speed than the speed of the substrate web. As the elastic ribbon is progressively bonded to the substrate web in the nip of a pair of sealing rolls, the elastic is stretched between its metering source and the sealing rolls. It is stretched an amount depending on the speed differential between the substrate web and the elastic ribbon metering rolls. This represents one of the simplest processes for combining elastics with moving webs.

Where tensioned elastics are applied in cross machine direction or at some other angle to machine direction, more complex systems have been required. For example, the substrate web may be passed through a festoon system whereby the continuously moving web is effectively indexed. That is, the substrate web is stopped for a short time along a portion of its path while the remainder of the web continues to move within a series of accumulation rolls. An elastic ribbon may then be sequentially stretched and bonded in any direction to the temporarily stationary portion of the web.

Where elasticity is desired in curved profiles, such as in elasticized diaper leg cuffs, even more complex processes have been required. For example, an elastic ribbon may be tensioned and then heat deactivated to cause it to become inelastic after it has been elongated. The inelastic ribbon may then be profiled, such as by camming the ribbon in a sinusoidal fashion perpendicular to machine direction as the ribbon is bonded to a substrate web. Because the elastic property is deactivated, the ribbon can be handled without concern for contraction forces disrupting the curved profile before and during bonding. Later, after the shaped elastic has been bonded to the substrate web, a separate heat reactivation step reestablishes the elasticity of the profiled ribbon. Because of the need for heat deactivation and reactivation, elastic material choices are limited. Such processes are complicated by the fact that whenever heat is applied to polymer elastic materials, the temperature must be accurately controlled to avoid interfering with elastic properties. Also, the important properties of spring rate and percent stretch that are available for heat reactivated elastic materials are less than those available for elastics which are not reactivated with heat.

Diaper elastic members are typically either polymer ribbons or laminates of multiple polymer strands combined with nonwoven sheets. Where an elastic member forms a continuous loop with no ends, the elastic member is defined as a garter. Elastic members may generally be bonded to substrates in high speed continuous processes by fusion-sealing, heat-activated adhesive sealing, or pressure sensitive adhesive sealing methods. These methods are more generally classified as thermal bonding and adhesive bonding.

Where a garter is stretched circumferentially and bonded to a substrate to create an elasticized opening, it may be necessary to remove substrate material from inside the garter if a hole was not first created in the substrate before bonding. Commercial processes for removing substrate material inside a garter have generally followed the steps of folding the substrate along a machine direction axis passing through the center of the pattern and then cutting out the substrate material inside the pattern by progressively cutting from the folded edge inward and then back to the folded edge. Although progressive cutting can be done at high speeds by rotary knives, by water jet, or by laser, these are all expensive converting processes. Also hole symmetry about the fold axis is generally required since both sides of a hole are cut simultaneously.

Diaper leg cuffs are often made by abutting two or more elasticized patterns which form less than a full loop. They are joined in order to create a full loop; however, such a composite loop does not have continuous elastics and therefore does not have the capability of distributing the stretch equally around the loop. Only continuous garter elastics have this capability, which is desired for optimum fit. Leg cuffs made by creating a tensioned garter are superior to leg cuffs made by other means of elasticization.

In light of the complexity of known processes for combining tensioned elastic members with moving substrates, and the need for generating diaper leg cuffs made of tensioned garters bonded to a moving substrate, it is an object of the present invention to combine tensioned garters with a continuously moving substrate in a process that simplifies stretching the garter in multiple directions and holding the tensioned garter in a predetermined shape while bonding it to the substrate.

It is a further object of the present invention to bond tensioned garters to a substrate while simultaneously creating a weakened zone at an edge of the garter bond for removal of the material inside the garter, without the need for folding the substrate or introducing external heat to the materials.

SUMMARY OF THE INVENTION

In one preferred embodiment, the present invention provides a method of combining a tensioned garter with a substrate. A tensioned garter is wrapped about a mandrel. The mandrel has a top surface and side walls depending from the top surface. The top surface has a perimeter defining a predetermined shape of the tensioned garter wrapped about the mandrel. The tensioned garter has an upper portion and a lower portion. A substrate is placed against the top surface of the mandrel. The substrate is secured to the tensioned garter while the tensioned garter is held by the mandrel in the predetermined shape. The securing step enables the tensioned garter to be stripped from the mandrel side walls when the substrate is moved away from the top surface of the mandrel. A portion of the substrate is removed from within the predetermined shape of the tensioned garter to form a hole around which the tensioned garter may contract.

In this preferred embodiment the upper portion of the tensioned garter is positioned above the top surface of the mandrel. The upper portion of the tensioned garter has sufficient tension to cause the upper portion of the garter to fold over onto the top surface of the mandrel to form a garter flange while the lower portion of the tensioned garter clings to the side walls of the mandrel. The step of securing the substrate to the tensioned garter in this embodiment includes passing the substrate, which lies against the garter flange, under an ultrasonic horn. The top surface of the mandrel acts as an anvil between which the ultrasonic horn presses the garter flange and the substrate together while applying vibration energy to form a fusion-seal therebetween. The top surface of the mandrel has a raised outer rim to provide a continuous fusion-seal at the outer rim. The outer rim has a shape against which the ultrasonic horn presses, which is adapted to weaken an edge of the continuous fusion-seal so that the edge of the fusion-seal which is weakened may be broken to remove from inside the fusion-seal a portion of the substrate and of the tensioned garter, thereby forming a hole around which a remaining portion of the tensioned garter may contract.

This embodiment further includes the step of stripping the tensioned garter from the mandrel while applying vacuum to the portion of the substrate inside the fusion-seal from the top surface of the mandrel so that the edge of the continuous fusion-seal is broken when the substrate and the remaining portion of the tensioned garter are stripped off the mandrel. The portion of the substrate broken away from the substrate is held by vacuum to the top surface of the mandrel until after the hole is completely formed in the substrate.

Another preferred embodiment of the present invention is similar to the first one except that the step of securing the substrate to the tensioned garter is altered. A hole is cut in the substrate prior to placing the substrate against the top surface of the mandrel. The hole has a shape smaller than the garter flange. The hole in the substrate is aligned with the mandrel so that the hole lies inside the garter flange. The substrate lying against the garter flange is passed under a sealing roll. The mandrel acts as an anvil against which the sealing roll presses the garter flange and the substrate. The garter flange is sealed to the substrate. The substrate may be secured to the tensioned garter by thermal sealing or adhesive sealing.

In another preferred embodiment of the present invention the step of securing the substrate to the tensioned garter is performed in a slightly different manner than previously set forth. The tensioned garter is positioned on the mandrel below the top surface and about the side walls of the mandrel. The side walls have recessed portions across which the tensioned garter spans. The substrate is backed with an anvil surface opposing the mandrel top surface. The tensioned garter is intercepted with sealing tools at locations where the tensioned garter spans the recessed portions of the side walls. The tensioned garter is pressed against the substrate backed by the anvil surface to enable securement of the tensioned garter to the substrate by a sealing means wherever pressing by the sealing tools occurs.

In yet another preferred embodiment, the present invention provides a method of making individual tensioned garters having a predetermined shape. A first tensioned elastic ribbon and a second tensioned elastic ribbon are metered tangentially toward a plurality of mandrels, each spaced apart by a gap along a common centerline. Each of the mandrels has a top surface and side walls depending therefrom. The first and second tensioned elastic ribbons are clamped between the mandrels by pushing the first tensioned elastic ribbon toward the common centerline and by pushing the second tensioned elastic ribbon toward the common centerline, thereby encircling the side walls of each of the mandrels as the first and second tensioned elastic ribbons meet at the common centerline. The first and second tensioned elastic ribbons are sealed together where they are clamped in order to form a ribbon seal between each of the mandrels. The first and second tensioned elastic ribbons are cut within the ribbon seal between each of the mandrels so that when cut, the tensioned elastic ribbons form individual tensioned garters about the side walls of each of the plurality of mandrels. The common centerline of mandrels may be wrapped circumferentially around a rotating drum so that the clamping step may occur progressively as the drum rotates. Also, each of the mandrels may be pivoted on radial shafts extending from the drum.

In this preferred embodiment the first and second tensioned elastic ribbons may be trilaminates having outer nonwoven layers and a plurality of elastic strands stretched longitudinally and intermittently bonded therebetween. The bonding of the plurality of elastic strands to the outer nonwoven layers is interrupted at unbonded locations equally spaced along the first and second tensioned elastic ribbons. The spacing of the unbonded locations corresponds to the gaps spacing apart the mandrels. Each of the first and second tensioned elastic ribbons at the unbonded locations is compressed sufficiently to cause the plurality of elastic strands between the outer nonwoven layers to burst and contract to where they are sealed without cutting the outer nonwoven layers, so that the unbonded locations have no elastic strands within them. and The unbonded locations of the first and second tensioned ribbons is registered to the gaps spacing apart the mandrels when the first and second tensioned elastic ribbons are metered tangentially toward the plurality of mandrels.

In yet another preferred embodiment, the present invention provides an apparatus for combining a tensioned garter with a substrate. The apparatus includes a mandrel having a top surface and side walls depending from the top surface. The apparatus also includes means for wrapping a tensioned garter about the mandrel. The top surface of the mandrel has a perimeter defining a predetermined shape of the tensioned garter. The tensioned garter has an upper portion and a lower portion. The apparatus also includes means for placing a substrate against the top surface of the mandrel and means for securing the substrate to the tensioned garter while the tensioned garter is held by the mandrel in a predetermined shape.

In this preferred embodiment the means for securing the substrate to the tensioned garter includes means for positioning the upper portion of the tensioned garter above the top surface of the mandrel. The upper portion of the tensioned garter has sufficient tension to cause the upper portion to fold over onto the top surface of the mandrel to form a garter flange while the lower portion of the tensioned garter clings to the side walls of the mandrel. The means for securing the substrate to the tensioned garter also includes means for sealing the substrate to the garter flange using the top surface of the mandrel as a sealing anvil. The means for sealing the substrate to the tensioned garter comprises an ultrasonic horn adapted to press against the sealing anvil with the substrate and the garter flange positioned therebetween. The ultrasonic horn applies vibration energy to form a fusion-seal between the substrate and the garter flange.

In this preferred embodiment there is a raised outer rim on the top surface of the mandrel. The raised outer rim provides a continuous fusion-seal at the outer rim. The outer rim has a shape against which the ultrasonic horn presses, which is adapted to weaken an edge of the continuous fusion-seal inside the fusion-seal so that the edge of the fusion-seal which is weakened may be broken. Breaking the weakened edge of the fusion-seal enables removing from inside the fusion-seal a portion of the substrate and of the tensioned garter to form a hole around which a remaining portion of the tensioned garter may contract. There is also means provided for stripping the tensioned garter from the mandrel while simultaneously applying vacuum to the portion of the substrate inside the fusion-seal from the top surface of the mandrel so that the weakened edge of the fusion-seal is broken when the substrate and the tensioned garter are stripped off the mandrel.

In still another preferred embodiment of the present invention therein is provided an apparatus for making individual tensioned garters having a predetermined shape. The apparatus includes a plurality of mandrels spaced apart along a common centerline, each of the mandrels having top surfaces and side walls depending therefrom. The apparatus includes means for metering a first tensioned elastic ribbon and a second tensioned elastic ribbon tangentially toward the plurality of mandrels. The apparatus includes means for clamping the first and second tensioned elastic ribbons between the plurality of mandrels by pushing the first tensioned elastic ribbon toward the common centerline and by pushing the second tensioned elastic ribbon toward the common centerline, thereby encircling the side walls of each of the mandrels as the first and second tensioned elastic ribbons meet at the common centerline. The apparatus includes means for sealing the first and second tensioned elastic ribbons together where they are clamped in order to form a sealed region between each of the plurality of mandrels and means for cutting through the first and second tensioned elastic ribbons within the sealed region between each of the plurality of mandrels so that when cut, the tensioned elastic ribbons form individual tensioned garters about the side walls of each of the plurality of mandrels. The common centerline of mandrels may be wrapped circumferentially around a rotating drum so that the clamping step may occur progressively as the drum rotates. Also, each of the mandrels may be pivoted on radial shafts extending from the drum.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

First Preferred Embodiment

Referring now to the drawings, and more particularly to FIGS. 1a-6, there is shown a first preferred embodiment of the present invention, which provides a method and apparatus for combining a tensioned elastic garter with a substrate, and is generally indicated as 30. Embodiment 30 includes a mandrel 32, which has a top surface 34 and side walls 36 depending from top surface 34. Top surface 34 is generally oval in shape, however top surface 34 may have any planar convex shape which has no concave portions. FIG. 1b shows top surface 34 to be substantially planar and that side walls 36 depend from the top surface 34 at an angle 37. Preferably, the angle 37 is at least 270°.

Figure 1A:
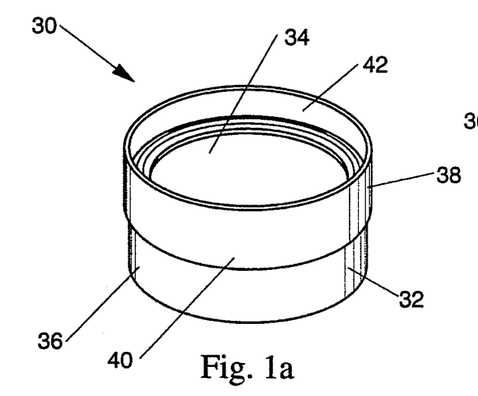
FIG. 1a is a simplified perspective view of a preferred embodiment of the method and apparatus for combining a tensioned elastic garter with a substrate of the present invention, disclosing a garter wrapped about an oval mandrel.
Figures 2, 3, 5:
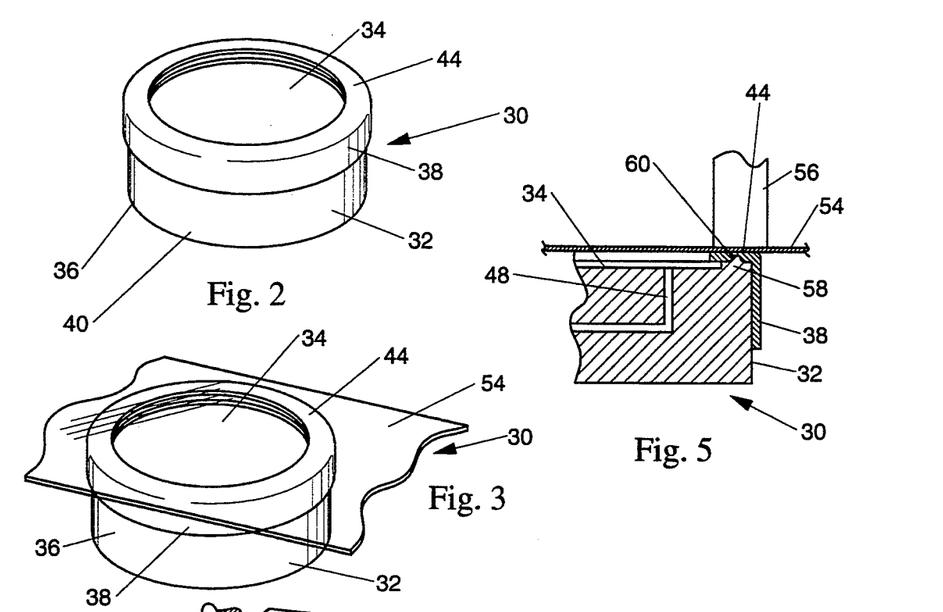
FIG. 2 is a simplified perspective view of the embodiment of FIG. 1a, showing the upper portion of the elastic garter folded over the top surface of the mandrel to form a garter flange.
FIG. 3 is a simplified perspective view of the embodiment of FIG. 2, showing a substrate brought into contact with the garter flange.
FIG. 5 is an enlarged partial front elevation section view, taken along section line 5—5 of FIG. 4, showing the interface between ultrasonic horn, substrate, tensioned elastic garter, and mandrel during the step of sealing the garter flange to the substrate and weakening the bond at the edge of the seal.

FIG. 1a shows a tensioned elastic garter 38 wrapped around mandrel 32. Elastic garter 38 has a lower portion 40 and an upper portion 42. Lower portion 40 clings tightly to side walls 36 of mandrel 32 due to the tension in the garter. FIG. 1a shows elastic garter 38 positioned with upper portion 42 above top surface 34 of mandrel 32. In this position, the tension in upper portion 42 of elastic garter 38 causes the upper portion 42 to fold onto top surface 34 in order to relieve some of the tension in upper portion 42, as shown in FIG. 2. Thus, FIG. 2 represents the stable condition of tensioned elastic garter 38 when it is positioned with its upper portion 42 above top surface 34 and its lower portion 40 wrapped around mandrel 32. In this condition upper portion 42 takes the form of an inward facing garter flange 44.

FIG. 3 shows a substrate 54 placed against the garter flange 44. Substrate 54 is shown as transparent for illustration purposes, but it may be made of any material which is sealable to the material of garter flange 44. Substrate 54 is preferably a nonwoven polypropylene. FIG. 3 shows substrate 54 in sheet form, but it may also be a continuous web. Garter 38 is preferably made of two nonwoven polypropylene strips, or one wide strip folded into two halves, which are bonded to multiple strands of elastic sandwiched between them by intermittent glue stripes. The elastic strands, not shown, are preferably parallel to one another and oriented circumferentially within the elastic garter. However, elastic garter 38 may also be a solid ribbon of elastic material, such as natural rubber, manufactured by Fulflex Company, located in Burlington, Vt.

Figure 4:
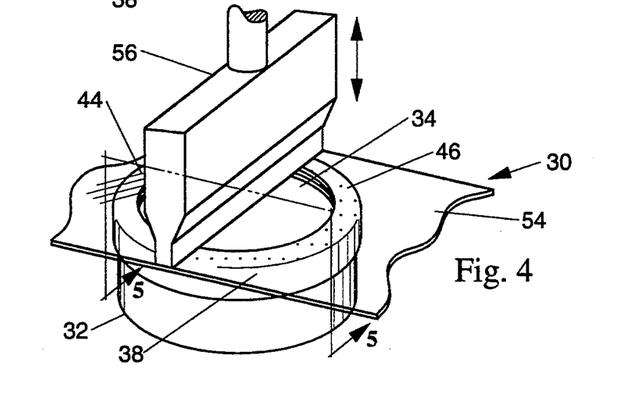
FIG. 4 is a simplified perspective view of the embodiment of FIG. 3, showing an ultrasonic horn bonding the substrate to the garter flange.

FIG. 4 shows an ultrasonic sealing horn 56 in contact with substrate 54 and positioned perpendicular to the top surface 34 of mandrel 32. Passing the top surface 34 of mandrel 32 under vibrating ultrasonic horn 56 enables ultrasonic horn 56 to progressively fusion-seal substrate 54 to garter flange 44, using top surface 34 of mandrel 32 as an anvil. Garter flange 44 and substrate 54 remain fixed relative to mandrel top surface 34 during the bonding process. Vibration energy, which melts the interface between substrate 54 and garter flange 44, is delivered by vibrating horn 56 from a source not shown. A fusion-seal 46 between garter flange 44 and substrate 54 is thereby generated.

Figure 1B:
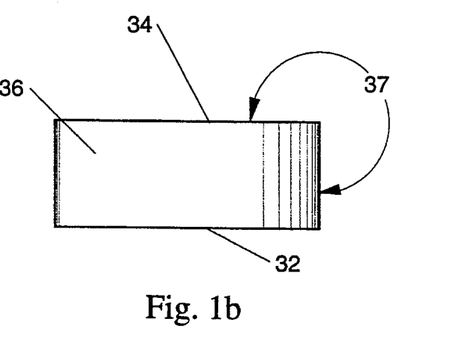
FIG. 1b is a front elevational view of the embodiment of FIG. 1a, without the garter, showing the angle between mandrel top surface and its depending side walls.

FIG. 5 shows the ultrasonic fusion bonding process in more detail. Mandrel 32 may preferably have a substantially planar top surface 34, as shown in FIG. 1b, if sufficient sealing energy can be applied to generate a seal the width of the garter flange. More preferably, top surface 34 has a raised outer rim 58 which extends above top surface 34. Rim 58 provides a focal point for ultrasonic vibration energy from horn 56 so that a fusion-seal 46 is formed between substrate 54 and garter flange 44 only where rim 58 supports garter flange 44.

An elastic garter may be bonded to a substrate with or without an opening inside the garter flange. It is preferable to have an opening around which the garter may contract. If an opening has been provided in the substrate prior to sealing, registration of the opening to the garter flange is required. More preferably an opening is created after sealing, and as part of the sealing process. Therefore, rim 58 preferably has a peak 60 at its upper surface, rising slightly above rim 58. Peak 60 acts to thin the seal between garter flange 44 and substrate 54. Where seal 46 is so thinned, it is weakened relative to the rest of the seal. Thus, outer rim 58 has a shape adapted to fusion-seal the garter flange 44 to the substrate 54, but with an edge of the seal weakened enough that material inside the continuous seal 46 can later be removed by stressing the weakened center enough to break it. Mandrel 32 is shown having a vacuum hole 48 connected to a vacuum source not shown. The purpose of vacuum hole 48 is discussed hereinafter.

Outer rim 58 and peak 60 are preferably continuous around the perimeter of top surface 34 of mandrel 32. If rim 58 were discontinuous, the seal between garter flange 44 and substrate 54 would also be discontinuous.

Having a discontinuous sealing pattern for an elastic garter, combined with a process for cutting the garter between seals, would enable attaching independently functional, tensioned elastics to a substrate in both machine direction and cross direction with one bonding step.

Figures 6, 7, 8, 9, 10:
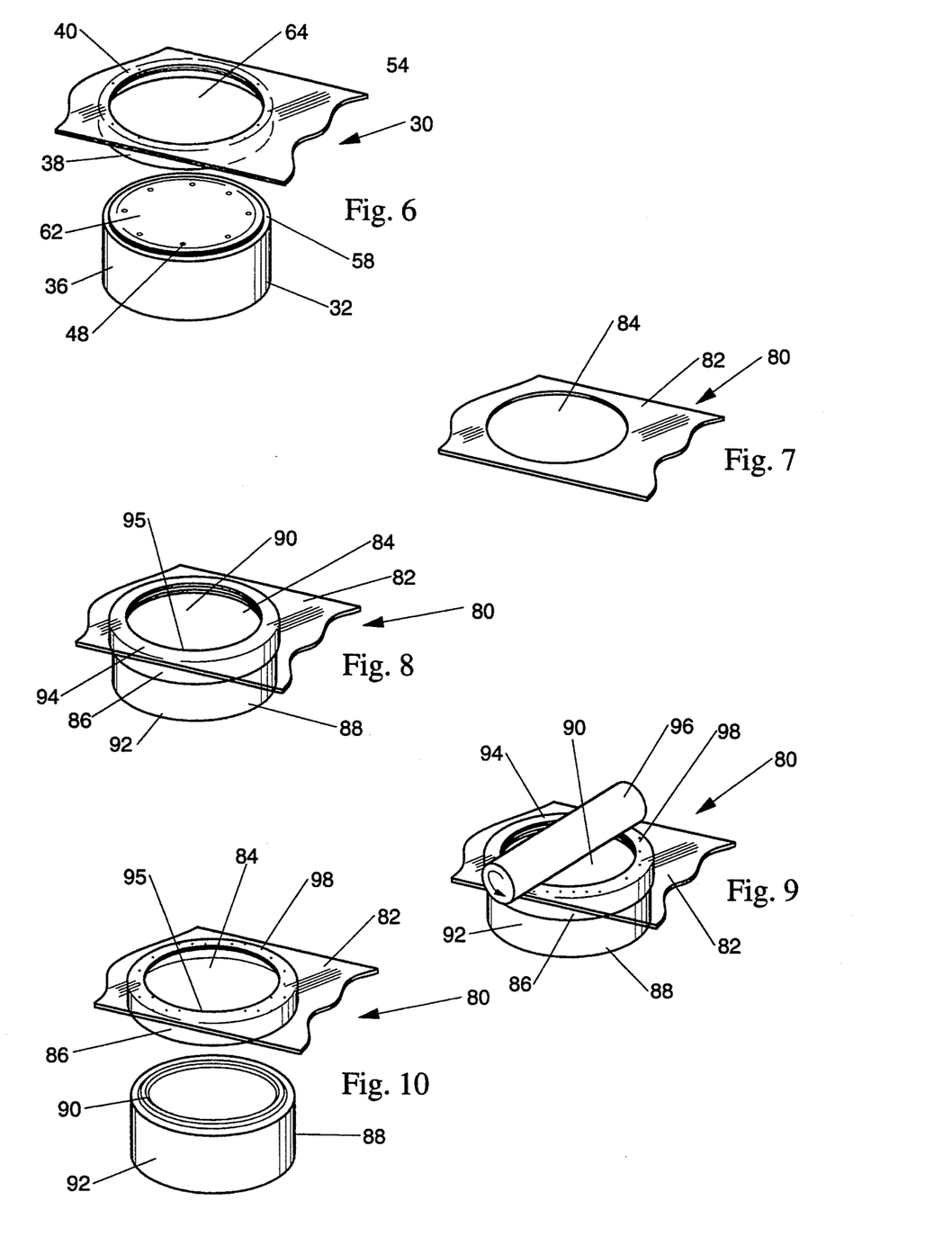
FIG. 6 is a simplified perspective view of the embodiment of FIG. 4, showing the substrate and garter stripped off the mandrel, while a portion of the substrate and a portion of the garter flange inside the garter are held to the mandrel by vacuum.
FIG. 7 is a simplified perspective view of an alternative embodiment of the method and apparatus for combining a tensioned elastic garter with a substrate of the present invention, disclosing a substrate having a pre-cut hole.
FIG. 8 is a simplified perspective view of the embodiment of FIG. 3, disclosing the substrate with pre-cut hole aligned with the garter flange formed on the mandrel.
FIG. 9 is a simplified perspective view of the embodiment of FIG. 8, disclosing a sealing roll bonding the substrate to the garter flange.
FIG. 10 is a simplified perspective view of the embodiment of FIG. 9, disclosing the stripping of the substrate and garter from the mandrel.

FIG. 6 shows the substrate 54 stripped from mandrel 32, carrying tensioned elastic garter 38 with it. The ultrasonic fusion-seal formed at rim 58 is strong enough to pull the lower portion 40 of garter 38 from side walls 36 when substrate 54 is lifted from top surface 34 of mandrel 32. The weakened part of fusion-seal 46 at peak 60 is weak enough that material 62, a portion of the substrate and of the garter flange inside the fusion-seal, is easily broken away from the strong part of the fusion-seal if material 62 is held against top surface 34 of mandrel 32 as the substrate 54 is stripped away. Material 62 is preferably held to top surface 34 by a vacuum from holes 48 in top surface 34, the source of which is not shown. By the process of simultaneously stripping the substrate 54 from the mandrel 32 and holding the material 62 to the mandrel, a hole 64 is created in substrate 54 around which tensioned garter 38 may contract, thereby forming an elasticized opening in substrate 54.

Second Preferred Embodiment

In FIGS. 7-10, them is shown a second preferred embodiment of the present invention, which provides a method and apparatus for combining a tensioned elastic garter with a substrate, and is generally indicated as 80. Embodiment 80 includes a mandrel and a sealing roll. It accommodates a substrate 82, which has a pre-cut hole 84, as is shown in FIG. 7.

FIG. 8 shows a garter 86 wrapped about a mandrel 88. Mandrel 88 has a top surface 90 which has side walls 92 depending therefrom, similar to the mandrel of the first embodiment. Garter 86 has a garter flange 94 folded onto the top surface 90 of the mandrel, similar to the first embodiment. Garter flange 94 has an innermost edge 95. Hole 84 in substrate 82 is sized to be slightly smaller in circumference than the innermost edge 95 of garter flange 94. Hole 84 may be aligned with innermost edge 95 when substrate 82 is placed against garter flange 94, as shown in FIG. 8.

FIG. 9 shows a rotatable sealing roll 96 in contact with substrate 82. Rolling contact between sealing roll 96 and the top surface 90 of mandrel 88 enables sealing roll 96 to progressively bond substrate 82 to a garter flange 94 to form seal 98, using mandrel top surface 90 as an anvil. Garter flange 94 and substrate 82 remain fixed relative to top surface 90 during this process. Sealing energy, which bonds the interface between substrate 82 and garter flange 94, may be delivered as heat and pressure by sealing roll 96, from a source not shown. Alternatively, a pressure sensitive adhesive layer, not shown, between substrate 82 and garter flange 94 may be activated by pressure alone from sealing roll 96. The material of elastic garter flange 94 may even be a pressure sensitive adhesive.

Indeed, there are many known bonding approaches which could be used to secure garter flange 94 to substrate 82. For example, sealing could be accomplished instantaneously rather than progressively by pressing a sealing die against the entire top surface 90 of mandrel 88. Top surface 90 of mandrel 88 may be substantially planar to maximize the seal area or for construction simplicity. Alternatively, mandrel 88 may have a raised outer rim, similar to outer rim 58 shown in FIG. 5, in order to minimize the seal area. Such an outer rim may be continuous in order to provide a continuous seal, or it may be discontinuous in order to achieve a discontinuous seal. Alternatively, a sealing die may have a continuous or discontinuous pattern pressing against a substantially planar mandrel top surface.

FIG. 10 shows substrate 82 sealed to a garter 86 being stripped from mandrel 88. The seal 98 between substrate 82 and garter flange 94 must be strong enough to enable stripping garter 86 from side walls 92 of mandrel 88.

Third Preferred Embodiment

Figure 11:
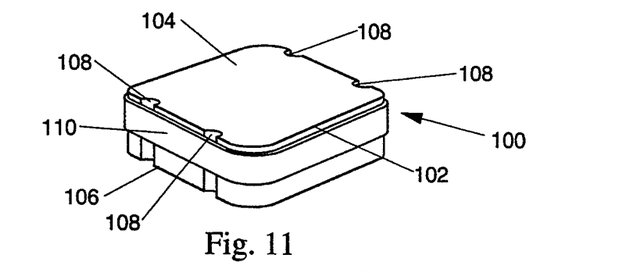
FIG. 11 is a simplified perspective view of an alternative embodiment of the method and apparatus for combining a tensioned elastic garter with a substrate of the present invention, disclosing a garter formed about a mandrel having recesses in its sides, and showing the garter spanning across the side recesses.

In FIGS. 11-14b, there is shown a third preferred embodiment of the present invention, which provides a method and apparatus for combining a tensioned elastic garter with a substrate, and is generally indicated as 100. Embodiment 100 includes a mandrel 102, which has a top surface 104 and side walls 106 depending from top surface 104. Top surface 104 may have any perimeter shape, as long as it has at least two concave portions formed by recesses 108 in side walls 106. FIG. 11 shows a mandrel 102 with four concave recesses 108. Top surface 104 is substantially planar and side walls 106 are substantially perpendicular to top surface 104.

FIG. 11 shows a tensioned elastic garter 110 wrapped around mandrel 102. Garter 110 clings tightly to side walls 106 of mandrel 102 due to the tension in the garter. The tension in garter 110 also causes garter 110 to span the concave recesses 108. FIG. 11 shows the entire elastic garter 110 positioned below top surface 104 of mandrel 102.

Figure 12:
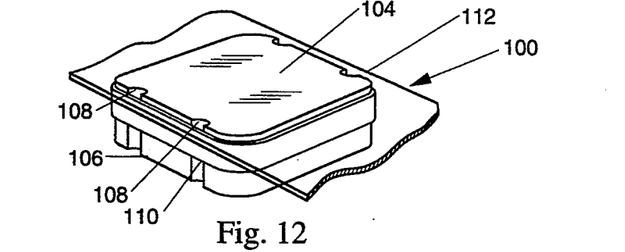
FIG. 12 is a simplified perspective view of the embodiment of FIG. 11, showing a substrate brought into contact with the top of the mandrel.

FIG. 12 shows a substrate 112 placed against the top surface 104 of mandrel 102. Substrate 112 is shown as transparent for illustration purposes, but may be any fabric or film which is sealable to the material of elastic garter 110. Garter 110 is made of preferably the same material as described for the first embodiment of the present invention. Substrate 112 is shown in sheet form, but it may also be a continuous web.

Figure 13A:
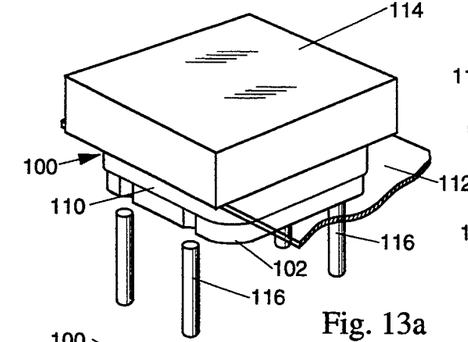
FIG. 13a is a simplified perspective view of the embodiment of FIG. 12, showing an anvil placed on top the substrate above the mandrel top surface, thereby sandwiching the substrate between the mandrel top surface and the anvil.
Figure 13B:
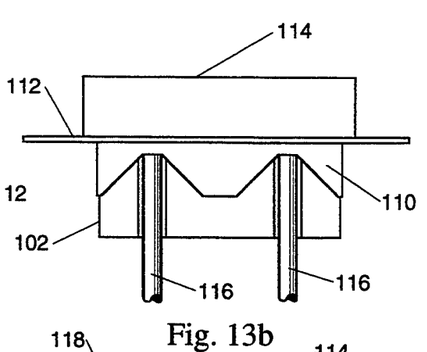
FIG. 13b is a front elevational view of the embodiment of FIG. 13a, showing sealing tools pushing the portion of the garter spanning the mandrel recesses upward against the substrate backed by the anvil.

FIGS. 13a and 13b show a substantially planar anvil plate 114 lowered into contact with substrate 112. Anvil plate 114 extends beyond the perimeter of top surface 104. Also shown are sealing tools 116 which rise through recesses 108 to intercept the portions of garter 110 which span across the recesses. Sealing tools 116 push garter 110 against substrate 112 which are backed by anvil plate 114. In order to prevent garter 110 from sliding off sealing tools 116, either the sealing surface of the tools is of sufficient size or spring-loaded guide pins, not shown, extend above the sealing surfaces of sealing tools 116 to contain garter 110. When garter 110 is pinched between the sealing tools 116 and substrate 112, garter 110 is gathered randomly by the sealing surfaces. Garter wrinkles are therefore sealed into the bond between garter 110 and substrate 112. Pressure sensitive adhesive, heat from sealing tools 116, heat from anvil 114, or a combination of them; as well as other adhesive or thermal bonding systems may act to create a bond 118 between garter 110 and substrate 112 at the points where sealing tools 116 press garter 110 and substrate 112 against anvil plate 114.

Figure 14A:
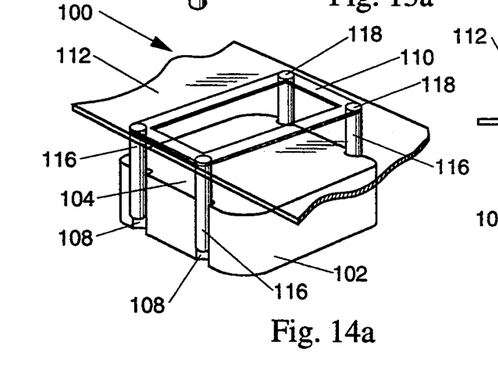
FIG. 14a is a simplified perspective view of the embodiment of FIG. 13a, showing the garter sealed to the substrate only at sealing tool locations, and the unsealed portions of the garter assuming straight line chords between seals after the garter and substrate are removed from the mandrel.
Figure 14B:
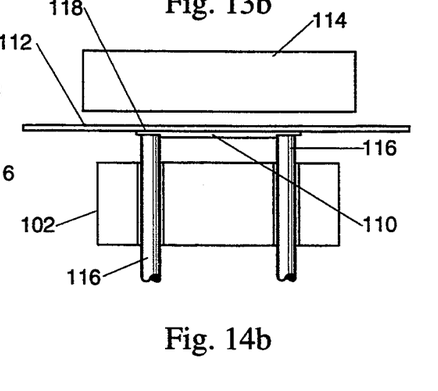
FIG. 14b is a front elevational view of the embodiment of FIG. 14a, showing the anvil removed and the sealing tools stripping the substrate and garter from the mandrel.

FIGS. 14a and 14b show anvil plate 114 removed after sealing, and sealing tools 116 stripping substrate 112 and garter 110 off mandrel 102. Portions of tensioned elastic garter 110, which are not sealed to substrate 112, take straight line paths between sealing points once the garter has been stripped off the mandrel, due to tension in the garter. Thus, a tensioned elastic pattern is generated, which is predetermined by the locations of recesses 108, but which may be different from the top surface perimeter of mandrel 102. That is, the mandrel shape is generally larger in circumference than the chordal lengths between recesses. Because the garter assumes a shape smaller than the circumference of the mandrel, some garter tension is removed after the substrate and garter are stripped from the mandrel.

Fourth Preferred Embodiment

Figure 15:
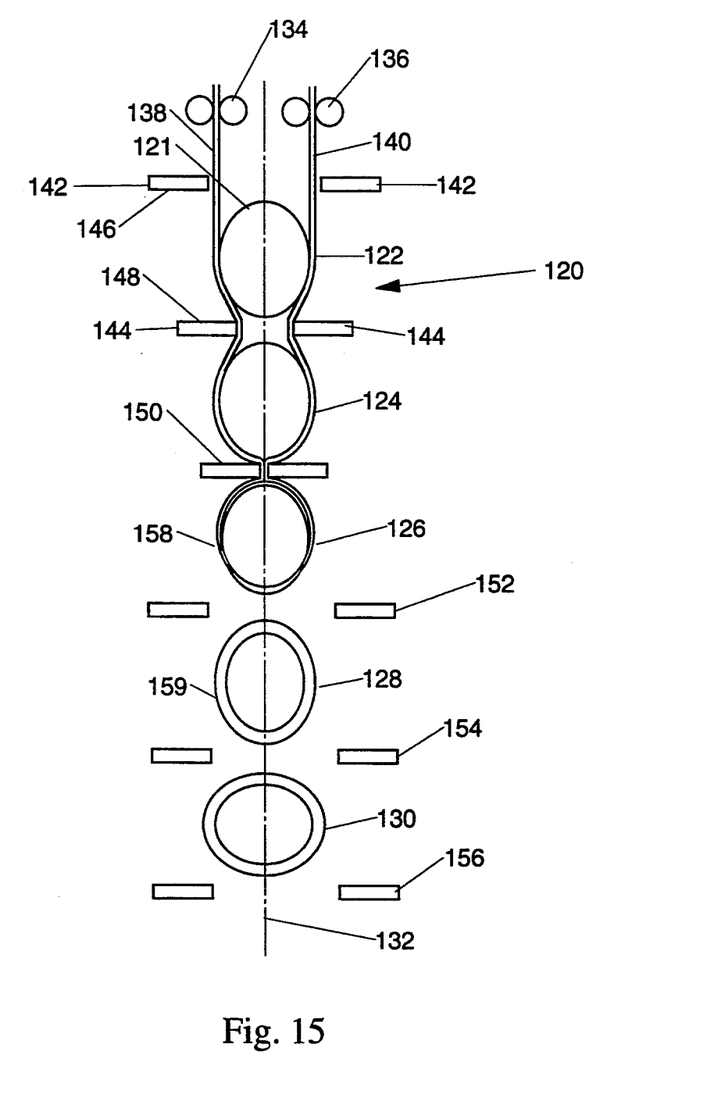
FIG. 15 is a top plan view of five mandrels having garters formed about them in a progressive fashion.
Figure 21A:
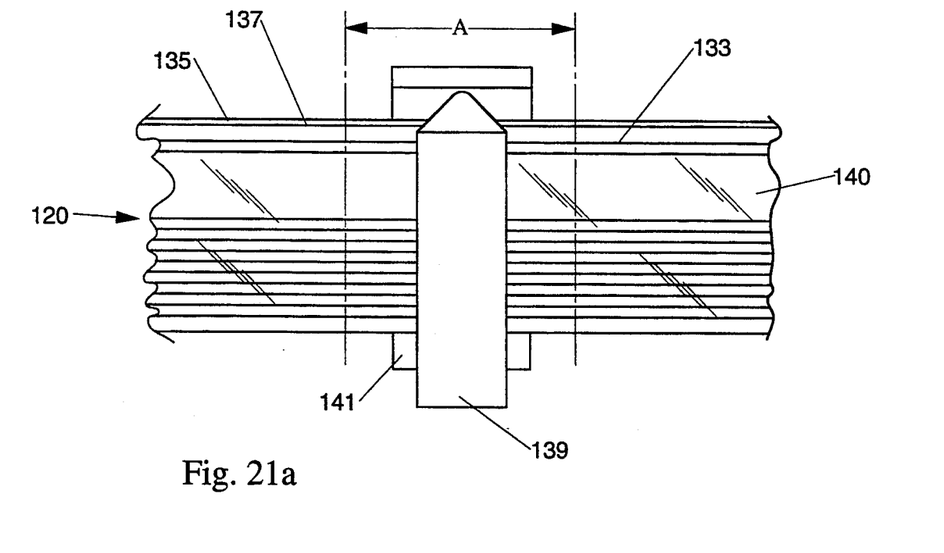
FIG. 21a is a simplified perspective view of an alternative embodiment of the method and apparatus of FIG. 15, showing a tensioned elastic ribbon being compressed between a blunt tool and an anvil surface.
Figure 21B:
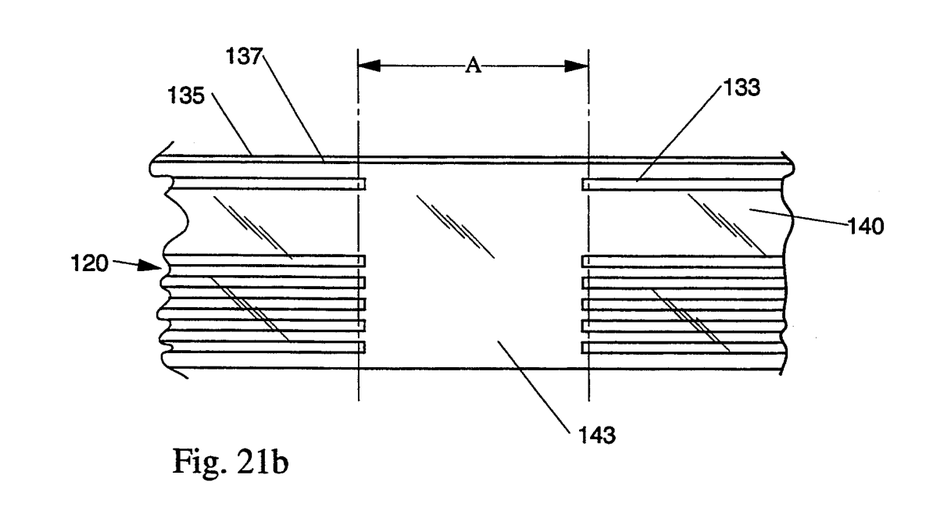
FIG. 21b is a simplified perspective view of the tensioned elastic ribbon of FIG. 21a, showing elastic strands within a small area of the tensioned elastic ribbon having been burst and contracted.

In FIGS. 15, 21a, and 21b there is shown a fourth preferred embodiment of the present invention, which provides a method and apparatus for forming a tensioned elastic garter around a mandrel, and is generally indicated as 120. Embodiment 120 includes an apparatus having a mandrel 121 shown in a series of five positions, designated 122, 124, 126, 128, and 130, all having a common centerline 132 and with substantially equal spaced gaps between mandrel positions. Mandrel 121 is preferably oval and similar to the mandrel design of the first preferred embodiment, as illustrated in FIGS. 1 and 2.

FIG. 15 shows two pair of metering rolls 134 and 136 located in a fixed position upstream of mandrel position 122. Metering roll pairs 134 and 136 feed elastic ribbons 138 and 140 respectively, tangentially to mandrel 121. As mandrel 121 is moved from its initial position 122 to position 124, the elastic ribbons 138 and 140 are stretched in a direction substantially parallel to the common centerline 132. Elastic ribbons 138 and 140 may be made as homogeneous sheets of elastic or laminates of elastic strands and nonwovens, or any other continuous webs of material capable of being stretched. Mandrels are either indexed from position to position or they move together at a constant speed.

Moving along with mandrel 121 are clamp pairs 142 and 144. Each clamp of the pair 142 also moves perpendicular to common centerline 132 in unison with its mate. Each clamp of the pair 144 moves similarly to those of pair 142 but at a different time in the process. Clamp pair 142 is shown open in position 146 outside the elastic ribbons 138 and 140, and clamp pair 144 is shown closing against the elastic ribbons, thereby pushing them toward common centerline 132 in position 148. When the mandrel 121 reaches position 124, clamp pair 142 moves to position 148 and clamp pair 144 moves to position 150.

Figure 20:
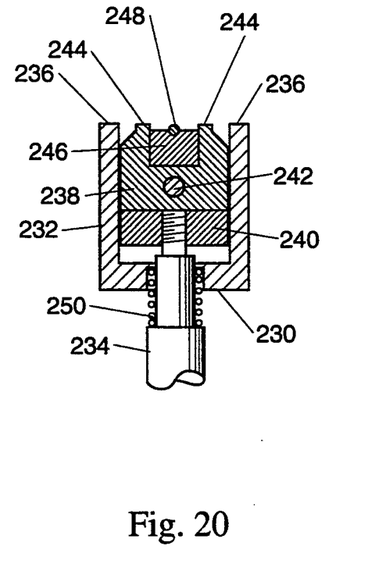
FIG. 20 is a sectioned plan view, taken along section line 20—20 of FIG. 17, showing the ribbon clamping, sealing, and cutting device.

As the mandrel 121 moves forward, the clamp pairs close on the elastic ribbons progressively until both ribbons are clamped at common centerline 132, as shown by clamp position 150. When each pair of clamps reach the closed position 150, elastic ribbons 138 and 142 are pressed against each other and sealed together by sealing means within the clamps. Also within each pair of clamps is a means for cutting the ribbon within the sealed region in order to separate the sealed elastic ribbon of one mandrel from that of the adjacent mandrel. A preferred clamp/seal/cut device is shown in FIG. 20. After remaining closed long enough for ribbon sealing and cutting, the closed clamp pairs open as shown in clamp position 152. Once opened, clamp pairs remain open as shown in subsequent positions 154 and 156.

In the clamp/seal/cut process of apparatus 120, the elastic ribbons 138 and 140 are progressively wrapped around the side walls of a mandrel to form a complete loop. At clamp position 150, the ribbons 138 and 140 are sealed and cut at the leading end of the mandrel in position 124 and at the trailing end of the mandrel in position 126. Thus, at mandrel position 126, a tensioned garter 158 is first formed. If the process of preferred embodiments one and two were used to generate a garter flange 159, garter flange 159 would be completely formed by mandrel position 128.

Elastic ribbons 138 and 140 may be metered in a partially contracted state at the speed of mandrel 121 traveling along common centerline 132. In this case the tension eventually applied to the ribbons would be a function of the amount of wrap applied to them around the mandrel 121. The ribbons may also be metered slower than the speed of mandrel travel such that stretch occurs during metering. Other tensioning arrangements are within the scope of the present invention as long as the garter has been tensioned some amount when formed around the mandrel.

At mandrel position 130 the oval mandrel is shown rotated 90°. Depending on the product application for the elastic garter, it may be required to have the oval garter oriented differently between the forming process and the downstream substrate securement process. A different mandrel orientation for garter forming may be desirable in order to minimize the amount of stretch imparted to the elastic ribbons as they are wrapped around the mandrel. When the elastic ribbon is metered parallel to the common centerline 132, less stretch is imparted during wrapping if the major axis of the oval is parallel to the common centerline 132 than if the major axis is perpendicular to the common centerline 132. Also, wrapping elastic ribbons around mandrels that are oriented such that there is minimum travel of the wrapping mechanism is important for high speed garter forming. FIG. 15 shows that if mandrel 121 is pivotable about its top surface center, it may be rotated at position 130 in order to meet both the garter forming and securement requirements.

FIGS. 21a and 21b show an alternative for elastic ribbon construction for the fourth preferred embodiment 120. Instead of a uniformly continuous elastic ribbon, the alternative ribbon preferably has unbonded locations which have no elastic in them, equally spaced along the length of each elastic ribbon. Such unbonded locations may be registered with the gaps between mandrels so that the ribbon sealing and cutting operations there do not have to seal and cut through elastic. If the tensioned elastic ribbons are made of a trilaminate of polypropylene nonwoven outer layers 135 and 137 and natural rubber elastic strands 133 bonded therebetween, it is preferable to avoid heat sealing through natural rubber, because the presence of such rubber weakens the seal between the two tensioned elastic ribbons bonded around the mandrels.

A trilaminate 140 made of nonwoven outer layers 135 and 137 and a plurality of natural rubber elastic strands 133 is preferably constructed by applying intermittently an adhesive to the stretched strands 133 when they are combined with the outer layers. In order to provide unbonded locations in the elastic ribbons, having a length A of about 1 to 3 inches (2.5 mm to 7.6 mm) long, in which there are no elastic strands, the laminate 140 is first bonded together with the unbonded locations having no adhesive applied. That is, stretched elastic strands 133 extend through each unbonded location, bonded at each side of the unbonded location but not bonded within it. Following such interrupted bonding, each tensioned elastic ribbon 138 or 140 is exposed to a compression process which bursts the elastic strands passing through each unbonded location.

In this process a blunt tool 139 presses against the trilaminate 140 backed by a substantially planar anvil surface 141. A fixed gap between tool 139 and anvil 141 of 0.001 inches (0.0025 mm) generates a localized pressure of 30,000 to 40,000 psi (2041 to 2722 atm.), which is sufficient to burst the plurality of natural rubber strands 133 without cutting the polypropylene nonwoven layers 135 and 137. Once the elastic strands 133 are burst, they contract to the edges of the unbonded location, leaving an unbonded location 143 in which there are no elastic strands passing through it.

Fifth Preferred Embodiment

Figure 16:
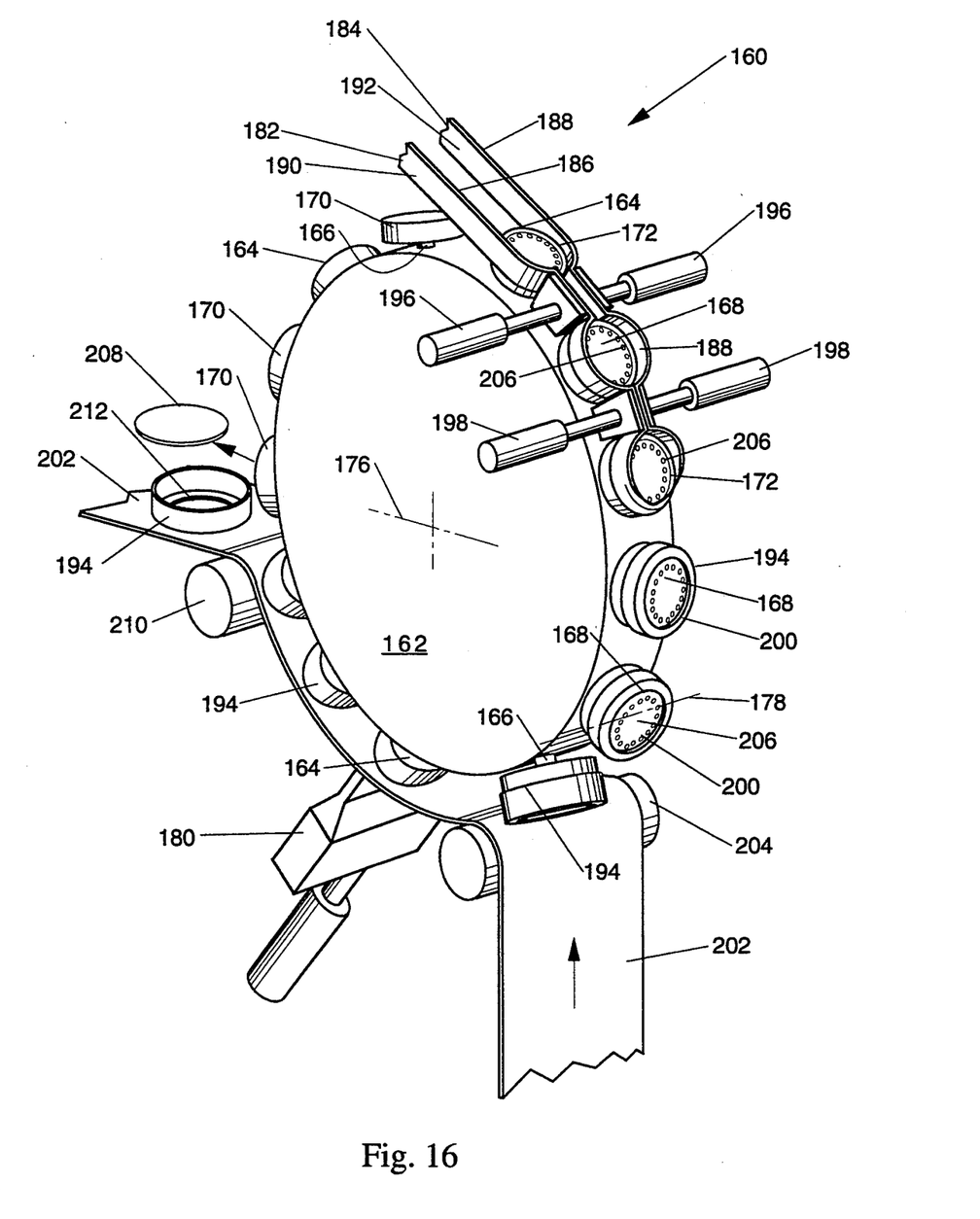
FIG. 16 is a perspective view of a rotating drum having mandrels spaced about it, illustrating a preferred apparatus and method of the present invention.

In FIG. 16, there is shown a fifth preferred embodiment of the present invention, which provides a method and apparatus for both forming and combining a tensioned elastic garter with a substrate, and is generally indicated as 160. Embodiment 160 includes a continuously rotating drum 162 supported and driven by a support means and drive means not shown. Mounted to drum 162 are oval mandrels 164 of the design described in preferred embodiment one. Mandrels 164 are connected to pivot shafts 166, which extend radially from drum 162, and they are equally spaced along a common centerline wrapped about the circumference of drum 162. In this configuration the garter forming process of preferred embodiment four and the combining process of preferred embodiment one are combined to operate continuously at high speeds, as is desirable for disposable diaper manufacturing.

Mandrels 164 have top surfaces 168 and side walls 170 similar to top surface 34 and side walls 36 of mandrel 32. Mandrels 164 also have raised outer rims 172 with beads 174 for ultrasonic bonding purposes, however outer rim 172 and peak 174 have top surface curvatures which permit their surfaces to remain tangential to an ultrasonic horn 180, which is externally mounted from drum 162, as the mandrels rotate past the stationary horn. Because the pivoting of mandrels 164 is desired as explained heretofor, the curvatures of outer rim 172 and peak 174 have an axis of curvature 176 coincident with the axis of rotation of the drum when the mandrels 164 are pivoted for ultrasonic horn engagement. The oval mandrels are pivoted such that their major axes of ovality 178 are parallel to curvature axis 176 when the mandrels 164 are pivoted for ultrasonic horn engagement. Elsewhere around the drum mandrels 164 are pivoted perpendicular to their orientation for ultrasonic horn engagement. In the latter orientation mandrels are oriented for formation of elastic garters about them.

FIG. 16 shows tensioned elastic ribbons 182 and 184 metered tangent to mandrel side walls 170. Tensioned elastic ribbons 182 and 184 have upper portions 186 and 188 and lower portions 190 and 192, respectively. Tensioned elastic ribbons 182 and 184 are metered such that when progressively wrapped around mandrels 164, upper portions 186 and 188 are positioned above top surface 168 of each mandrel. Garters 194 are created by the method of the fourth preferred embodiment of the present invention; i.e., progressively clamping ribbons 182 and 184 together between mandrels, and then sealing and cutting the ribbons between the mandrels. The elastic ribbons are preferably made with unbonded locations having no elastic rubber strands passing through them, as described in preferred embodiment four, so that sealing and cutting between mandrels is optimized.

FIG. 16 shows successive mandrels 164 having elastic ribbons 182 and 184 progressively pushed together by clamp pairs 196 and 198, which are operated by air cylinders mounted to drum 162. Although clamp pairs operate between each mandrel, only two clamp pairs are shown in FIG. 16 for clarity. Air may be delivered to a manifold for air cylinder operation through a rotary joint at the drum axis of rotation and thereafter valved and exhausted to and from cylinders, as is commonly known in the art. A stationary manifold shoe may be placed against the side walls of the rotating drum to deliver air under pressure at the appropriate time in the drum cycle, as is also commonly known in the art. Alternatively, clamping mechanisms may have ball screw drives, or they may be cam operated, or a combination of air pressure and camming may be used for actuation.

As explained for the first preferred embodiment of the present invention, upper portions 186 and 188 of elastic ribbons 182 and 184 fold over onto raised outer rims 172 of mandrels 164 so that when garters 194 are wrapped about mandrels 162, garter flanges 200 are also formed, due to the tension in upper portions 186 and 188. Meanwhile, lower portions 190 and 192 of tensioned elastic ribbons 182 and 184 cling to the side walls 170 of mandrels 164 to hold the garters in place for garter-to-substrate sealing.

After garter formation, oval mandrels 164 may be rotated 90° about their pivot shafts 166. A substrate web 202 is thereafter introduced tangentially to the circumference of drum 162 by passing it over roll 204. Substrate web 202 travels at the same speed as outer rims 172 of mandrels 164 past stationary ultrasonic horn 180. As mandrels 164 pass ultrasonic horn 180, the ultrasonic horn vibrates radially to drum 162, pressing substrate 202 and garter flange 200 together against mandrel rim 172 of each passing mandrel. Outer rims 172 preferably have peak surfaces, not shown, against which ultrasonic horn 180 presses in order to fusion-seal the garter flange 200 to the substrate 202 with a weakened seal edge inside the oval bond. The vibrational energy is transmitted to the interface of the substrate 202 and garter flange 200 generating a continuous fusion-seal wherever rim 172 supports the substrate and garter flange as an anvil surface. At the peak surfaces the fusion-seal is thinned to a glassine state, thereby weakening an edge of the fusion-seal.

Once a fusion-seal is formed between substrate 202 and garter flange 200, vacuum is applied to the top surface 168 of mandrel 164 through holes 206 from a vacuum source not shown. As with air delivery, fixed external manifolds sliding against drum side walls or rotary joints may be employed to deliver vacuum, as is commonly known in the drum and turret machine art.

The vacuum pulls a portion of substrate 208 inside the oval fusion-seal against top surface 168 of the mandrel 164. During the application of vacuum, substrate 202 passes over another roll 210. The path of substrate 202 away from drum 162 acts to strip garters from the side walls 170 of mandrels 164 while vacuum holds substrate portion 208 against top surface 168. The action of stripping the substrate from the mandrel while holding the material inside the garter to the mandrel breaks the weakened edge of the fusion-seal such that a substrate hole 212 is formed inside the garter 194.

A portion of the garter flange 200 inside the fusion-seal remains attached to substrate portion 208 which continues to be held by mandrel vacuum after stripping. Once stripping is complete, vacuum is exhausted and compressed air blown through holes 206 to eject substrate portion 208. Substrate portion 208 is collected by a scrap removal system not shown. Mandrel 164 is then pivoted 90° to its garter forming position so that the cycle may be repeated about drum 162.

Figure 17:
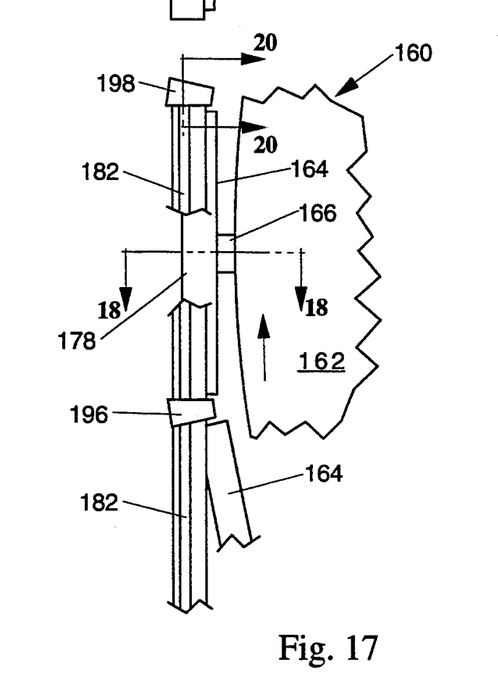
FIG. 17 is a side elevational view of a mandrel mounted to a rotating drum, illustrating the tangential elastic ribbon metering and clamping process of FIG. 16.

FIG. 17 shows a partial side view of drum 162 illustrating the tangential feeding of an elastic ribbon 182 to side walls 170 of mandrels 164. Each mandrel has a pivot shaft 166 connecting mandrel 164 to drum 162. Pivot shafts 166 extend radially from drum 162 and are driven by means not shown. Such means may be individual shaft motors, for example, or a gear train driven from a stationary ring gear inside the drum. Such drives are well known in the art.

The drum process embodiment illustrated by FIG. 16 could also be applied to preferred embodiment two if ultrasonic horn 180 were replaced with sealing roll 96.

Figures 18, 19:
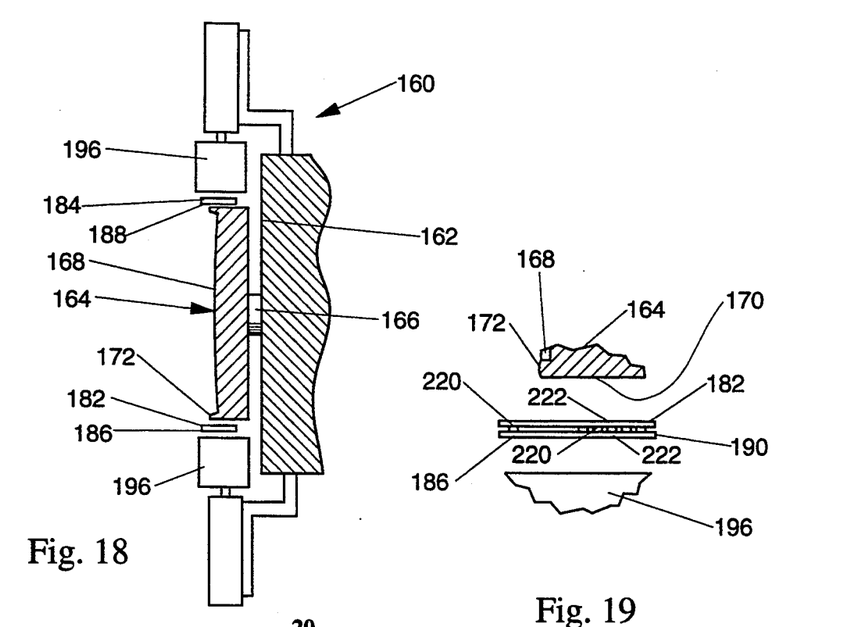
FIG. 18 is a sectioned front elevational view, taken along section line 18—18 of FIG. 17, showing elastic ribbons entering between mandrel and clamps.
FIG. 19 is an enlarged partial view of FIG. 18, showing a preferred elastic ribbon construction located relative to the mandrel.

Clamp pairs 196 and 198 are illustrated by trapezoids located between mandrels in FIG. 17. FIG. 18 shows a partial cross-section of drum 162, illustrating clamp pair 196 and its air cylinders supported from the drum and elastic ribbons 182 and 184 adjacent mandrel 164 prior to clamping. Elastic ribbons 182 and 184 have upper portions 186 and 188 respectively, positioned above top surface 168 and outer rim 172 of mandrel 164.

FIG. 19 is an enlarged view to better illustrate the position of elastic ribbon 182 relative to mandrel 164. Also shown in FIG. 19 is the preferred construction of the elastic ribbons. Elastic ribbon 182 has a single strand of elastic 220 sandwiched between two webs of nonwoven 222 at its upper portion 186. At its lower portion 190, elastic ribbon 182 has five strands of elastic 220 sandwiched between the two webs of nonwoven 222. This arrangement provides sufficient tension in upper portion 186 to cause the upper portion 186 to fold over onto the outer rim 172 and top surface 168 of mandrel 164 when the ribbon is wrapped around the mandrel. It also provides sufficient tension in lower portion 190 to cling to the side walls 168 of mandrel 164. The gap between the bottom five elastic strands and the top elastic strand provides space for sealing garter flange 200 to substrate 202 without sealing through the elastic strands.

FIG. 20 is a cross-section of one clamp 230 of clamp pair 196 to illustrate the mechanism that clamps, seals, and cuts elastic ribbons 182 and 184. Clamp 230 has yoke 232 slidably supported on stepped air cylinder rod 234. The end surfaces 236 of yoke 232 are the clamping surfaces. Inside yoke 232 is a sealing die 238 connected to air cylinder rod 234 via insulating block 240. Sealing die 238 has a cartridge heater 242 energized by a source not shown. Sealing die 238 has two sealing surfaces 244 which are pressed against the elastic ribbons 182 and 184 after the ribbons are clamped by end surfaces 236. A compression spring 250 biases yoke 232 outward such that clamping surfaces 236 are initially positioned slightly beyond sealing surfaces 244. Between sealing surfaces 244 is an insulating block 46 supporting a nichrome wire 248. The clamping force is a function of spring compression while sealing force is a function of air cylinder pressure. The opposing sealing die of each pair has a flat heated sealing block instead of separate sealing surfaces 244 and nichrome wire 248. Nichrome wire 248 is energized from a source not shown to cause it to heat above the melt temperature of the elastic ribbons and thereby cut the elastic ribbons within the sealed region. When the sealing dies are retracted, elastic ribbons 182 and 184 remain sealed together on either side of the heated nichrome wire. When the clamps are opened by further retraction of the air cylinders, the sealed ribbons snap to their respective mandrels.

Exemplary Construction of the Fifth Preferred Embodiment

The elastic ribbons 182 and 184 of the present invention are preferably a trilaminate construction as shown in FIG. 19. The width of outer layer 222 is 1.88 inches (47.75 mm), and it is made of polypropylene nonwoven. There are six elastic strands 220 spaced approximately as shown, and they are about 2.5 mm in diameter unstretched, and made of natural rubber. The laminate may have two separate web pieces or have one piece of web 222 folded in half at the bottom portion. The laminate is bonded together intermittently by pressure sensitive adhesive. The laminate preferably has a 130 percent elongation when fully stretched.

The drum 162 of the present invention has 18 mandrels 164, each mounted at a 13 inch (330 mm) pitch distance about the drum. Each mandrel 164 has a major oval dimension of 11.70 in. (297.2 mm) and a minor oval dimension of 8.88 in. (223.5 mm). There is a 1.3 inch (33 mm) gap between adjacent mandrels. Mandrels are preferably made of steel with a hardened top surface. Each mandrel has a top surface 168 and side walls 170 depending therefrom at an angle of about 285° so that the lower portion of garter 194 clings to the mandrel side walls without slipping off as tension in the upper portion of garter 194 forms the garter flange 200. The ribbons 182 and 184 are positioned relative to the mandrels such that the top surface 168 lies about midway between the upper portion elastic strand and the closest bottom portion elastic strand within the laminate.

As shown in FIG. 16, the oval mandrels preferably have their major axes aligned parallel to the mandrel travel during garter formation. The elastic ribbons are preferably metered by rubber on steel metering roll pairs (not shown) at the mandrel tangential speed or slightly faster so that the percent elongation imparted to each of them is slightly less than their 130% limit when the garter is formed around the mandrel. The 2.5 inch (63.5 mm) bore ribbon sealing air cylinders are pressurized to about 80–90 psig (5.4–6.1 mm.) and press the sealing dies against elastic ribbons 182 and 184 across their width to seal them. Die temperature is about 160° C. and sealing time is approximately 0.1 seconds. The 0.062 inch (1.575 mm) diameter nichrome wire is heated to 165°–170° C. The clamp force is about 3.4 pounds (15.1 Newtons). Sealing dies are made of C18400 chrome copper and have surfaces coated with electroless nickel codeposited with teflon to a 0.0003–0.0005 inch (0.0076–0.0127 mm) thickness.

Mandrels 164 are rotated 90° after garter forming in order to position the oval major axis 178 perpendicular to the direction of mandrel travel for desired substrate bonding orientation.

Substrate 202 is a 25 grams/square yard polypropylene nonwoven of 19 in. width, which is metered under 100 grams/lineal inch (39 gm/cm) tension tangentially to and at the same speed as curved mandrel top surfaces 168. This tangential speed is preferably 320 feet/minute (1626 mm/sec). Mandrel 164 has raised continuous outer rim 172, which is 0.100 in. (0.254 mm) above top surface 168 and 0.100 in. (0.254 mm) in width. Ultrasonic horn 180 is mounted tangentially to the mandrel top surface path, which has a radius of curvature of 37.53 inches (953.26 mm). The horn has a flat surface 0.64 inches (16.26 mm) wide in the direction of drum travel. The ultrasonic system has a vibration frequency is 20,000 Hertz and a horn interference setting of 0.005 inches 0 0.127 (mm). Contact time is approximately 0.01 seconds and maximum power output is used from a model no. 180P ultrasonic power source, available from Branson Ultrasonic Co. of Danbury, Conn.

Outer rim 172 has continuous peak 174 at its center to weaken the fusion seal at that point by compressing the substrate and garter flange very thin. The sealing surface has two angled surfaces blended with a 0.03 inch (0.76 mm) radius curved surface between them. The angled surfaces are both at about 12°–15° from horizontal toward the base of the rim 172.

In order to remove the portion of the substrate and garter flange 208 from inside the oval seal, a 20 inches of water (508 mm of H2O) vacuum is applied to the substrate at the top surface 168 of the mandrel after sealing has been completed. This vacuum is sufficient to hold portion 208 while substrate web 202 is pulled over roll 210 and away from the mandrel 164. The bond between substrate 202 and garter flange 200 outside the weakened edge is sufficient to pull the garter with the substrate off the mandrel.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method of combining a tensioned garter with a substrate, said method comprising the steps of:
   a) wrapping a tensioned garter about a mandrel, said mandrel having a top surface and side walls depending from said top surface, said top surface having a perimeter defining a predetermined shape of said tensioned garter wrapped about said mandrel, said tensioned garter having an upper portion and a lower portion, said upper portion of said tensioned garter being positioned above said top surface of said mandrel, said upper portion of said tensioned garter having sufficient tension to cause said upper portion of said tensioned garter to fold over onto said top, surface of said mandrel to form a garter flange while said lower portion of said tensioned garter clings to said side walls of said mandrel;
   b) placing a substrate against said garter flange; and
   c) passing said mandrel having said substrate lying again said garter flange under an ultrasonic horn said top surface of said mandrel having a raised outer rim to provide a continuous fusion-seal at said outer rim, said outer rim having a shape against which said ultrasonic horn presses while applying vibration energy to also weaken an edge of said continuous fusion-seal inside said continuous fusion-seal, so that said edge of said continuous fusion-seal which is weakened may later be broken to remove from inside said continuous fusion-seal a portion of said substrate and of said tensioned garter, thereby forming a hole around which a remaining portion of said tensioned garter may contract.

2. The method of claim 1 further comprising the step of:
   d) stripping said tensioned garter from said mandrel while applying vacuum to said portion of said substrate inside said continuous fusion-seal from said top surface of said mandrel so that said edge of said continuous fusion-seal is broken when said substrate and said tensioned garter are stripped off said mandrel, said portion of said substrate being held by vacuum to said top surface of said mandrel until after said hole is completely formed in said substrate.

3. An apparatus for combining a tensioned garter with a substrate, said apparatus comprising:
   a) a mandrel having a top surface and side walls depending from said top surface;
   b) means for wrapping a tensioned garter about said mandrel, said top surface of said mandrel having a perimeter defining a predetermined shape of said tensioned garter, said tensioned garter having an upper portion and a lower portion, said upper portion of said tensioned garter being positioned above said top surface of said mandrel said upper portion of said tensioned garter having sufficient tension to cause said upper portion of said tensioned garter to fold over onto said top surface of said mandrel to form a garter flange while said lower portion of said tensioned garter clings to said side walls of said mandrel;
   c) means for placing a substrate against said garter flange;
   d) means for passing said top surface of said mandrel under an ultrasonic horn, said top surface of said mandrel acting as a sealing anvil; and
   e) an ultrasonic horn which presses against said sealing anvil with said substrate and said garter flange positioned therebetween, said ultrasonic horn applying vibration energy to form a fusion-seal between said substrate and said garter flange.

4. The apparatus of claim 3 further comprising a raised outer rim on said top surface of said mandrel, said raised outer rim providing a continuous fusion-seal at said outer rim, said outer rim having a shape against which said ultrasonic horn presses to weaken an edge of said continuous fusion-seal inside said continuous fusion-seal so that said edge of said continuous fusion-seal which is weakened may be broken to remove from inside said continuous fusion-seal a portion of said substrate and of said tensioned garter, forming a hole around which a remaining portion of said tensioned garter may contract.

5. The apparatus of claim 4 further comprising means for stripping said tensioned garter from said mandrel while simultaneously applying vacuum to said portion of said substrate inside said continuous fusion-seal from said top surface of said mandrel so that said weakened edge of said continuous fusion-seal is broken when said substrate and said tensioned garter are stripped off said mandrel.

* * * * *

UNITED STATES PATENT AND TRADEMARK OFFICE
CERTIFICATE OF CORRECTION

PATENT NO. : 5,393,360
DATED : February 28, 1995
INVENTOR(S) : Russell P. Bridges, James R. Golan, Ronald H. Helton
Stephen J. Lange, Michael J. Madill, Michael G. Nease It is certified that error appears in the above-identified patent and that said Letters Patent is hereby corrected as shown below:

*Column 17, Claim 1 a), line 48, after "top" delete --,--.*

*Column 17, Claim 1 c), line 54, delete "again" and insert therefore --against--.* line 54, after "horn" insert a --,--.

Signed and Sealed this

Twenty-eighth Day of September, 1999

Attest:

Q. TODD DICKINSON

*Attesting Officer*  *Acting Commissioner of Patents and Trademarks*